United States Patent
Suzuki et al.

(10) Patent No.: US 7,199,160 B2
(45) Date of Patent: Apr. 3, 2007

(54) ANTIOBESTIC AGENTS AND HEALTH FOODS

(75) Inventors: Kazuo Suzuki, Tokyo (JP); Shigekazu Nakajima, Tokyo (JP); Shinji Yano, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 23 days.

(21) Appl. No.: 10/432,877

(22) PCT Filed: Oct. 9, 2001

(86) PCT No.: PCT/JP01/08847

§ 371 (c)(1),
(2), (4) Date: Oct. 30, 2003

(87) PCT Pub. No.: WO02/43761

PCT Pub. Date: Jun. 6, 2002

(65) Prior Publication Data

US 2004/0067215 A1   Apr. 8, 2004

(30) Foreign Application Priority Data

Nov. 28, 2000 (JP) ............................. 2000-361835
Feb. 15, 2001 (JP) ............................. 2001-037938

(51) Int. Cl.
- *A01N 33/12* (2006.01)
- *A61K 31/14* (2006.01)
- *A61K 31/74* (2006.01)

(52) U.S. Cl. .................. 514/643; 424/78.01; 424/78.1; 424/78.16; 514/909; 514/911

(58) Field of Classification Search ............ 424/78.01, 424/78.1, 78.16; 514/643, 909, 911
See application file for complete search history.

(56) References Cited

U.S. PATENT DOCUMENTS

| | | | |
|---|---|---|---|
| 4,765,994 A | | 8/1988 | Holmgren |
| 5,286,481 A | * | 2/1994 | Weisenfeld ............... 424/78.01 |
| 5,380,522 A | * | 1/1995 | Day ..................... 424/78.08 |
| 5,447,726 A | * | 9/1995 | Nomura ................... 424/464 |
| 5,980,881 A | * | 11/1999 | Mitsuka et al. ............ 424/78.1 |

FOREIGN PATENT DOCUMENTS

| | | |
|---|---|---|
| JP | 5-186356 | 7/1993 |
| JP | 11-147828 | 6/1999 |
| WO | 92/08469 | 5/1992 |
| WO | 97/36927 | 10/1997 |

OTHER PUBLICATIONS

Katsuhiko Tokunaga, "Himan wo Gappei shita Kou-Ketsuatsusou no Chiryou", Prog. Med., vol. 20, No. 10, Oct. 20, 2000, pp. 1979 to 1982 (hereinafter "the Tokunaga article"), (together with an English translation of its relevant portions in a Rule 131 Declaration).

A. Must et al., "The Disease Burden Associated with Overweight and Obesity", JAMA, vol. 282, No. 16, pp. 1523-1529, Oct. 27, 1999.

Third Report of the National Cholesterol Education Program (NCEP) Expert Panel on Detection, Evaluation, and Treatment of High Blood Cholesterol in Adults (Adult Treatment Panel III), pp. 1-27, May 2001.

Obesity in the United states Workforce, Findings from the National Health and Nutrition Examination Surveys (NHANES) III and 1999-2000, pp. 1-12, Dec. 2004.

Jean-Pierre Despres et al., "Effects of Rimonabant on Metabolic Risk Factors in Overweight Patients with Dyslipidemia", The New England Journal of Medicine, vol. 353, No. 20, pp. 2121-2134, Nov. 17, 2005.

S. J. Nicholls et al., "Effects of Obesity on Lipid-Lowering, Anti-Inflammatory, and Antiatherosclerotic Benefits of *Atorvastatin* or *Pravastatin* in Patients with Coronary Artery Disease (from the REVERSAL Study)", Am. J. Cardiol., vol. 97, pp. 1553-1557, 2006.

D. B. Hunninghake et al., "Comparative Effects of Simvastatin and Atorvastatin in Hypercholesterolemic Patients with Characteristics of Metabolic Syndrome", Clinical Therapeutics, vol. 25, No. 6, pp. 1670-1686, 2003.

* cited by examiner

*Primary Examiner*—Patrick Lewis
(74) *Attorney, Agent, or Firm*—Wenderoth, Lind & Ponack, L.L.P.

(57) ABSTRACT

Antiobestic agents and health foods containing as the active ingredient substances having an effect of adsorbing bile acid in the digestive tract, an effect of inhibiting intestinal circulation or an effect of inhibiting the absorption of exogenous lipids typified by pharmaceutically acceptable anion exchange resins. In particular, antiobestic agents and health foods characterized by lowering body weight and/or visceral fat content without reducing food intake.

12 Claims, 2 Drawing Sheets

ANTIOBESTIC AGENTS AND HEALTH FOODS

This application is a U.S. national stage of International Application No. PCT/JP01/08847 filed Oct. 9, 2001.

TECHNICAL FIELD

The present invention relates to an antiobesity agent and a health food, each containing as an active ingredient a substance having an action of adsorbing bile acids in the digestive tract, an action of inhibiting enterohepatic circulation, or an action of suppressing absorption of exogenous lipids, which reduce body weight and/or visceral fat levels without decrease of food consumption.

BACKGROUND

Hyperlipidemia and diabetes are considered as the highest risk factor of atherosclerosis, and treatment of obesity is believed to improve these conditions. Obesity treatment is normally based on dietetic treatment. However, the development of a medicament or a health food has been desired that reduces body weight and visceral fat levels without decrease of food consumption.

An anion exchange resin, which is known as a cholesterol lowering agent including colestimide as a typical example (trade name: Cholebine, Mitsubishi Pharma Corporation), is known to adsorb bile acids in the intestine to excrete the acids into feces, and inhibits reabsorption of the bile acids from the intestine. Accordingly, in the liver, conversion of cholesterol to bile acids (catabolism of cholesterol) is promoted, and as a result, blood LDL cholesterol is uptaken into the liver to supply cholesterol as a raw material, whereby blood cholesterol levels are decreased in humans and various animals. Particularly as for colestimide, it has been reported that colestimide exhibits high adsorption ability to cholic acid, as well as to all the constitutive lipids in bile acid-lipid complex micelles consisting of cholic acid, oleic acid, monooleyl glycerol, phospholipid (lecithin+lisolecithin), and cholesterol [Pharmacology and Therapy (Yakurito-chiryo), 24 (Suppl. 4): 601, 1996].

As for the aforementioned Cholebine, the resin was described as applicable to dieting on pages 150 to 153 and 186 to 189 in "Brilliant postmenopausal life—the secret of youthfulness: An advise of hormonotherapy" (Oct. 20, 2000, Kabushiki Kaisha Maeda Shuppan). Specifically, this report describes that during the course of dietetic treatment, some people fail dieting because they eat between meals and cannot decrease food consumption, but they can reduce their weight by the use of Cholebine. However, what is described in the article is a method to perform dieting by taking Cholebine before a meal to allow the resin to swell up in the stomach so as to maintain the feeling of fullness in the stomach, which results in the decrease of food consumption. In other words, the report merely describes that food consumption is decreased by utilizing the feeling of fullness achieved by Cholebine, so as to reduce body weight. As for as the inventors are aware, no report has been made on reduction of body weight and/or visceral fat levels without decrease of food consumption, as intended by the present invention.

Accordingly, an object of the present invention is to provide a novel method for reducing body weight and/or visceral fat levels without decrease of food consumption.

DISCLOSURE OF THE INVENTION

The inventors of the present invention conducted various studies to achieve the foregoing objective. As a result, they found that substances that have an action of adsorbing bile acids in the digestive tract, an action of inhibiting intestinal circulation, or an action of suppressing absorption of exogenous lipids, which are represented by pharmaceutically acceptable anion exchange resins including colestimide (2-methylimidazol-epichlorohydrin copolymer) known as a cholesterol lowering agent, reduce body weight and/or visceral fat levels without decrease of food consumption. The present invention was achieved on the basis of the above findings.

The gist of the present invention thus relates to an antiobesity agent which comprises as an active ingredient a substance having an action of adsorbing bile acids in the digestive tract, an action of inhibiting intestinal circulation, or an action of suppressing absorption of exogenous lipids. A preferred embodiment relates to reduction of body weight and/or visceral fat levels without decrease of food consumption.

The second gist of the present invention includes a pharmaceutical composition for prophylactic and/or therapeutic treatment of obesity which comprises an active ingredient a substance having an action of adsorbing bile acids in the digestive tract, an action of inhibiting intestinal circulation, or an action of suppressing absorption of exogenous lipids. A preferred embodiment of the present invention includes a pharmaceutical composition for prophylactic and/ or therapeutic treatment of obesity, which is characterized to reduce body weight and/or visceral fat levels without decrease of food consumption.

The third gist of the present invention includes a health food, which contains a substance having an action of adsorbing bile acids in the digestive tract, an action of inhibiting intestinal circulation, or an action of suppressing absorption of exogenous lipids. A preferred embodiment of the present invention relates to reduction of body weight and/or visceral fat levels without decrease of food consumption.

Other aspects of the present invention include a method of reducing body weight without decrease of food consumption by using a substance having an action of adsorbing bile acids in the digestive tract, an action of inhibiting intestinal circulation, or an action of suppressing absorption of exogenous lipids; and a method of decreasing visceral fat levels without decrease of food consumption by using a substance having an action of adsorbing bile acids in the digestive tract, an action of inhibiting intestinal circulation, or an action of suppressing absorption of exogenous lipids.

Preferred embodiments of the present invention include the inventions wherein a substance having an action of adsorbing bile acids in the digestive tract, an action of inhibiting intestinal circulation, or an action of suppressing absorption of exogenous lipids is a pharmaceutically acceptable anion exchange resin; the inventions wherein the pharmaceutically acceptable anion exchange resin is selected from colestimide, cholestyramine resin, colestipol, colesevelam hydrochloride, and sevelamer hydrochloride; and inventions wherein the pharmaceutically acceptable anion exchange resin is an anion exchange resin synthesized by polymerization reaction of an epichlorohydrin derivative with an amine. More preferable embodiments include the inventions wherein the pharmaceutically acceptable anion exchange resin is colestimide.

BEST MODE FOR CARRYING OUT THE INVENTION

Figure 1:
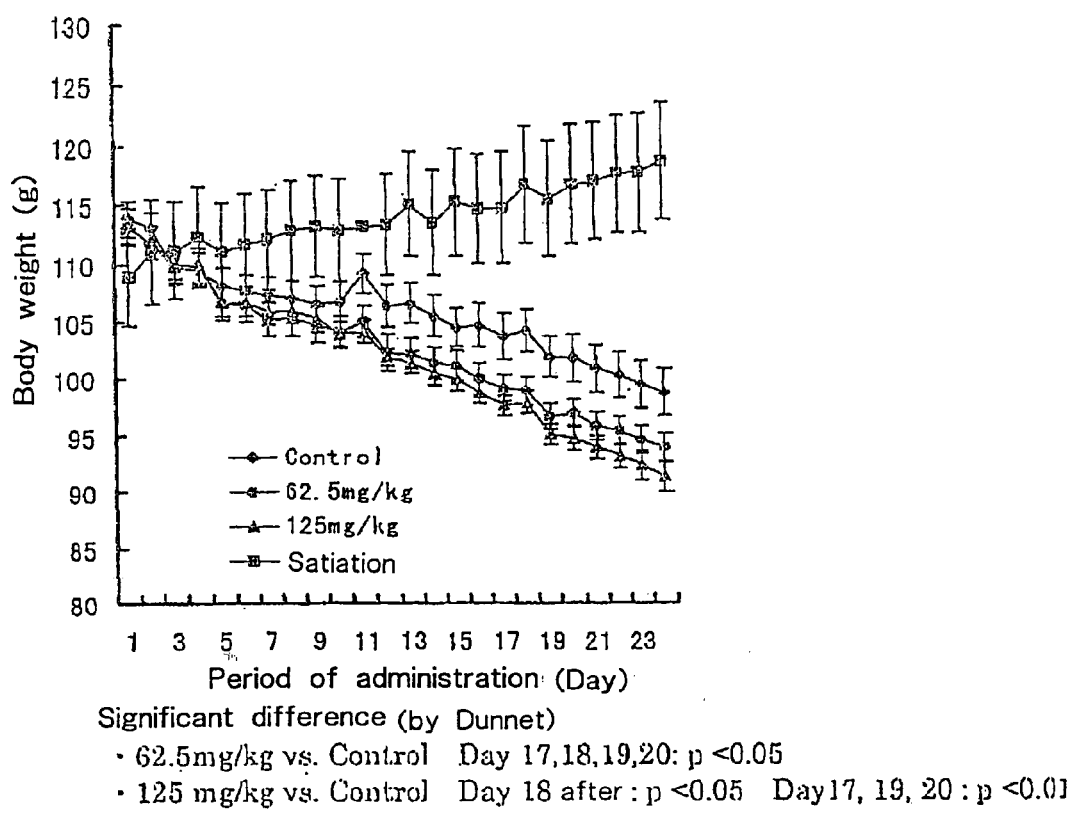
FIG. 1 shows the effect of administration of colestimide on body weight used in the example.

The present invention will be explained in more detail.

According to the present invention, a substance having an action of adsorbing bile acids in the digestive tract, an action of inhibiting intestinal circulation, or an action of suppressing absorption of exogenous lipids is used. The substance is not particularly limited, so far that the substance has the aforementioned action. Preferably, as shown in the following examples, the substance has an action of reducing body weight and/or visceral fat levels without decrease of food consumption. An example of these substances is a pharmaceutically acceptable anion exchange resin. An example of the pharmaceutically acceptable anion exchange resin includes colestimide (2-methylimidazole-epichlorohydrin copolymer) (also known as colestilan) as a most preferred example. Colestimide has an irregularly assembled and complicated stereostructure, and is represented by the fundamental structure of the following formula (I) that is partially represented by the following formula (II). The resin is obtained by the polymerization reaction of an epichlorohydrin derivative with an amine including an imidazole derivative as a typical example, more specifically by the production method described in Japanese Patent Unexamined Publication (Kokai) No. 60-209523.

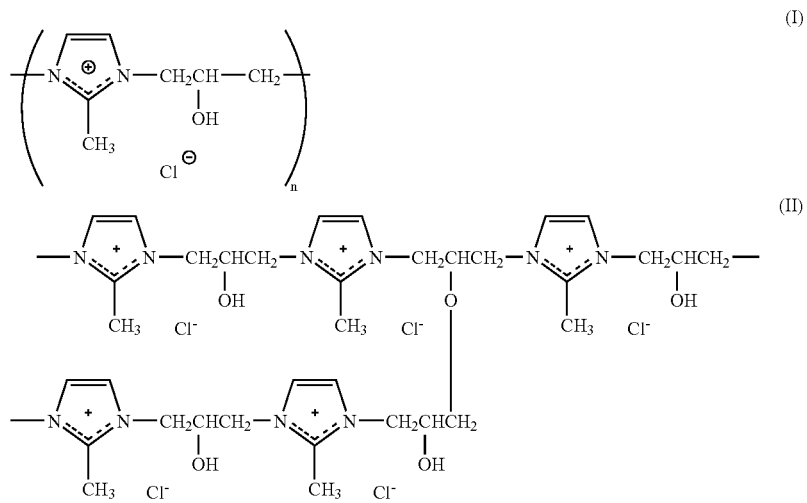

Examples of other preferable anion exchange resins include the above cholestyramine resin, and colestipol ((chloromethyl)oxirane-added N-(2-aminoethyl)-N'-[2-[(2-aminoethyl)amino]ethyl]-1,2-ethanediamine polymer), which are sold by SIGMA. The cholestyramine resin is a strongly basic anion exchange resin containing styrene-divinylbenzene copolymer added with quarternary ammonium groups, and its fundamental structure is represented by the following formula (III).

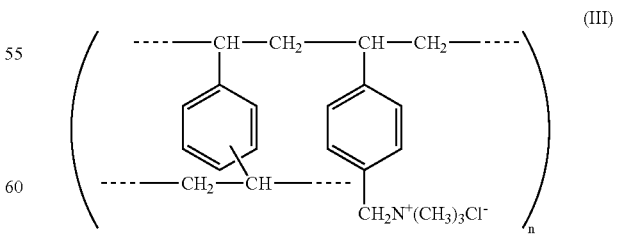

The fundamental structure of colesevelam hydrochloride is represented by the following formula (IV), and the resin can be produced by the method of U.S. Pat. No. 5,607,669 or a similar method thereto.

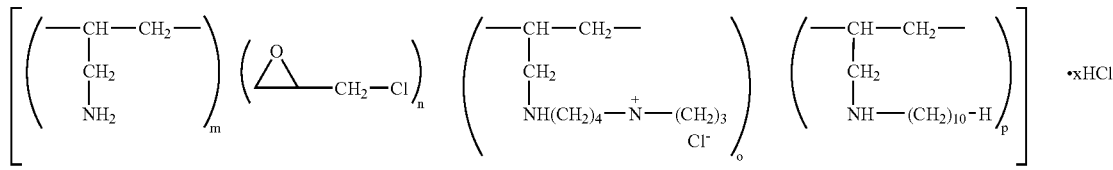

The fundamental structure of sevelamer hydrochloride is represented by the following formula (V), and the resin can be produced by the method of U.S. Pat. No. 5,496,545, or a similar method thereto.

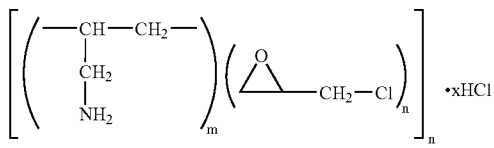

In addition, anion exchange resins described in Japanese Patent Publication of International Application (Kohyo) Nos. 9-504782, 9-500368, 10-501264, 10-501842, 11-507093, 11-512074, and 5-512332, and Japanese Patent Unexamined Publication (Kokai) Nos. 8-208750, 9-202732, 10-114661, and 11-228449 can also be used in the present invention, as long as they are not beyond the gist of the present invention.

The above compound an active ingredient, per se, can be used as the antiobesity agent and the health food of the present invention. It is preferred that a pharmaceutical composition and a health food containing the above active ingredient is manufactured by using an widely-used additive for pharmaceutical preparation, and then use the same.

Examples of the pharmaceutical composition and the health food include tablets, capsules, subtle granules, pills, troches, and liquids, and these are orally administered. In addition, when applied as a health food, the good may be in the form of a confectionary.

The pharmaceutical composition and health food for oral administration can be manufactured by a conventional method widely used, such as mixing, filling or compressing. Further, by applying repeated formulation procedures, the active ingredient may be distributed in a pharmaceutical composition or a health food containing a large amount of excipient. For example, tablets or capsules used for oral administration are preferably provided as unit dosage forms, and they may contain ordinarily used carriers for pharmaceutical preparation, such as a binder, excipient, diluent, compressing agent, lubricant, disintegrator, coloring agent, flavoring agent, and moistening agent. A tablet may be manufactured as a coated tablet according to a well known method in the art by using a coating agent, for example.

Examples of a preferable excipient include cellulose, mannitol, and lactose. Starch, polyvinylpyrrolidone, starch derivative including sodium starch glycolate or the like as a disintegrator, and sodium lauryl sulfate or the like as a lubricant can be used as additives for the pharmaceutical preparation. Orally-available pharmaceutical compositions and health foods in the form of a liquid are provided as, for example, a pharmaceutical composition or a health food, such as an aqueous or oil suspension, a solution, an emulsion, a syrup, or an elixir; or a dry pharmaceutical composition or a health food which can be re-dissolved in water or an appropriate medium before use.

In the liquids, commonly used additives may be added such as, for example, a precipitation preventing agent, such as sorbitol, syrup, methyl cellulose, gelatin, hydroxyethylcellulose, carboxymethylcellulose, aluminum stearate gel, or hydrogenated edible fat; an emulsifier such as lecithin, sorbitan monooleate, or gum arabicum; oily esters such as almond oil, refined coconut oil, or glycerin esters; a non-aqueous medium such as propylene glycol, or ethyl alcohol (edible oils may be included); a preservative such as methylester, ethyl ester, or propyl ester of p-hydroxybenzoic acid, or sorbic acid; and an optionally ordinarily used flavoring agent or coloring agent.

The above pharmaceutical composition and the health food for oral administration such as in the forms of tablets, capsules, or subtilized granules generally contain 5 to 95% by weight, preferably 25 to 90% by weight of the active ingredient.

The colestimide has been sold by Mitsubishi Pharma Corporation as a trade nam of "Cholebinein", and Cholebine may be used, per se, for the present invention.

Dose of the antiobesity agent of the present invention may appropriately be determined depending on the age, health conditions, and body weight of a patient, severity of disease, a type of simultaneous therapy or treatment, a nature of desired effects and the like. In general, a dose per day for an adult may be 1 to 60 g as a weight of an active ingredient, and the agent may be administered once or several times a day. Further, when a health food is applied, an amount can be appropriately determined based on the above dose.

EXAMPLES

The present invention will be specifically explained by referring to the examples. However, the present invention is not limited to these examples. The colestimide used below was prepared by the production method described in Japanese Patent Unexamined Publication (Kokai) No. 60-209523.

Example 1

(Experimental Method)

Golden Syrian hamsters (male, clean, 8-week old, Japan Laboratory Animals, Inc.) were housed in the individual cage. Food containing 2% cholesterol (MF: oriental yeast+ 2% cholesterol) was administered, and food intake in a satiation state was measured. After 1 week, the hamsters were divided into 4 groups (n=8/group) so that the hamsters of each group had uniform weights.

Satiation state was maintained for Group 1 (satiation group). The other 3 groups to be administered with the same amount of food were administered once a day with food in a unified amount (4.2 g/hamster) that corresponded to 70% of the average food intake per day in the satiation state.

The three groups administered with the same amount of food were forcedly and orally administered with water (control group), or with 62.5 mg/kg of colestimide, or 125 mg/kg of colestimide as a drug once a day before feeding for 24 days. The satiation group was remained unadministered.

Each dose of colestimide per body weight of a hamster was suspended in 10 mL of water when administered.

(Measured Items)

After 24 days of administration as described above, portal blood, abdominal vena cava blood, intrahepatic fat, and intra-abdominal fat (visceral fat) were collected from the satiation group, control group, 62.5 mg/kg colestimide-administered group and 125 mg/kg colestimide-administered group under ether anesthesia. Further, fat in the visceral organs was collected, and the wet weight was measured. In addition TC (total cholesterol), TG (triglyceride), PL (phospholipid), and FFA (free fatty acid) in portal blood and vena cava blood were respectively measured as serum lipid by a standard method.

(Results)

It was confirmed that all 3 groups administered with food in the same amounts ate all the food everyday, which corresponded to 70% of the food intake in the satiation state. The habit of storing food common in hamsters was not observed.

(1) Body Weight Change

As shown in FIG. 1, the body weight of the satiation group was slightly and gradually increased. Whilst, the body weight of the control group was gradually reduced, and on day 24, the weight was reduced by 15.0 g on the average. The colestimide-administered groups also gave reduced body weight in a dose-related manner (−19.2 g in the 62.5 mg/kg colestimide-administered group, and −22.8 g in the 125 mg/kg colestimide-administered group), and the groups constantly gave body weight lower than that of the control group throughout the experimental period. From day 17, both of the drug-administered groups gave significant body weight reduction compared to the control group.

(2) Visceral Fat Weight

Figure 2:
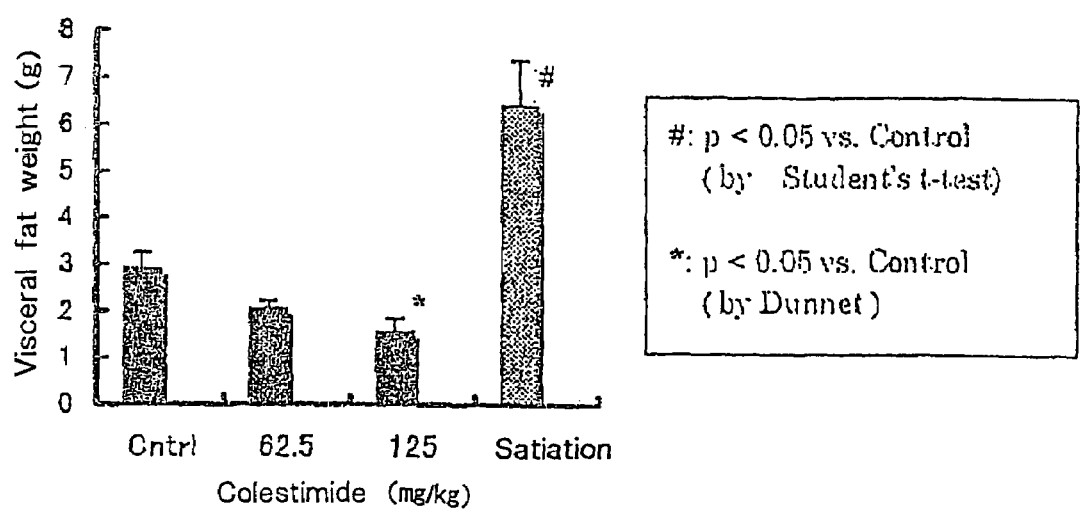
FIG. 2 shows the effect of administration of colestimide on visceral fat weight used in the examples.

As shown in FIG. 2, as compared to the visceral fat weight (6.39 g) of the satiation group, the control group gave a 54.5% decrease (2.91 g). Dose-dependent decreases were observed in the colestimide-administered groups, i.e., 29.9% in the 62.5 mg/kg colestimide-administered group and 46.0% in the 125 mg/kg colestimide-administered group.

(3) Serum Lipids

TC, TG, and FFA in the blood of the whole body obtained from the vena cava were decreased insignificantly by the administration with colestimide. PL was significantly decreased in the high dose (125 mg/kg)-administered group, in comparison with the control group. Whilst, the satiation group gave significantly higher values than the control group except for PL. The effect on serum lipids is shown below.

TABLE 1

Effect on serum lipids (venous blood)

| Group | TC, mg/dL | TG, mg/dL | PL, mg/dL | FFA, μM eq. |
|---|---|---|---|---|
| Satiation group | 377.3 ± 18.4 | 156.5 ± 18.4 | 233.9 ± 8.5 | 1524.2 ± 55.9 |
| Control group | 247.2 ± 8.8## | 53.8 ± 5.0## | 274.7 ± 5.0 | 1370.3 ± 88.9 |
| 62.5 mg/kg-administered group | 233.3 ± 13.8 | 51.9 ± 4.8 | 250.4 ± 10.2 | 1278.4 ± 81.3 |
| 125 mg/kg-administered group | 221.7 ± 9.3 | 43.9 ± 4.4 | 240.0 ± 5.1** | 1310.3 ± 98.3 |

Mean ± SE
$p < 0.01$ vs. satiation group
**$p < 0.01$ vs. control group (Dunnett's multiple test)

It was verified from the above results that colestimide had an antiobesity action to reduce cholesterol levels as well as reduce body weight and visceral fat levels when used in combination with dietetic treatment.

In the above experiment, after food intake in the satiation state was measured, food that corresponded to 70% by weight of the food intake (4.2 g/hamster) was supplied once a day. All the hamsters completely ate the food by the next day and no food remained uneaten, so that differences in food intake due to administration with colestimide were successfully excluded.

Thus, it can be concluded that reduced body weight and visceral fat weight observed in the colestimide-administered groups were not derived from decreased food intake, but occurred by adsorption of bile acids (inhibition of intestinal circulation) in the digestive tract or suppression of absorption of exogenous lipids.

These results revealed that body weight and/or visceral fat levels can be reduced by administration of colestimide without decrease of food consumption.

INDUSTRIAL APPLICABILITY

According to the present invention, a novel antiobesity agent and a health food is successfully provided that can reduce body weight and/or visceral fat levels without decrease of food consumption.

The present application was filed based on Japanese Patent Application Nos. 2000-361835 and 2001-37938 on which priorities are claimed.

What is claimed is:

1. A method for treating obesity without a decrease of food consumption, which comprises orally administering to a subject in need thereof an effective amount of a pharmaceutically acceptable anion exchange resin, wherein the pharmaceutically acceptable anion exchange resin is administered in the form of a capsule, tablet, granule or pill, and wherein the subject does not decrease the subject's food consumption.

2. The method according to claim 1, wherein the pharmaceutically acceptable anion exchange resin is selected from colestimide, cholestyramine resin, colestipol, colesevelam hydrochloride, and sevelamer hydrochloride.

3. The method according to claim 1, wherein the pharmaceutically acceptable anion exchange resin is synthesized by a polymerization reaction of an epichlorohydrin derivative with an amine.

4. The method according to claim 1, wherein the pharmaceutically acceptable anion exchange resin is colestimide.

5. The method according to claim 1, wherein the pharmaceutically acceptable anion exchange resin is administered for the sole purpose of reducing obesity.

6. The method according to claim 1, wherein the pharmaceutically acceptable anion exchange resin is the sole active ingredient administered.

7. A method for reducing a body weight of a subject without a decrease of food consumption, which comprises orally administering to a subject in need thereof an effective amount of a pharmaceutically acceptable anion exchange resin, wherein the pharmaceutically acceptable anion exchange resin is administered in the form of a capsule, tablet, granule or pill, and wherein the subject does not decrease the subject's food consumption.

8. The method according to claim 7, wherein the pharmaceutically acceptable anion exchange resin is selected from colestimide, cholestyramine resin, colestipol, colesevelam hydrochloride, and sevelamer hydrochloride.

9. The method according to claim 7, wherein the pharmaceutically acceptable anion exchange resin is synthesized by a polymerization reaction of an epichiorohydrin derivative with an amine.

10. The method according to claim 7, wherein the pharmaceutically acceptable anion exchange resin is colestimide.

11. The method according to claim 7, wherein the pharmaceutically acceptable anion exchange resin is administered for the sole purpose of reducing obesity.

12. The method according to claim 7, wherein the pharmaceutically acceptable anion exchange resin is the sole active ingredient administered.

* * * * *